(12) United States Patent
Mitzner

(10) Patent No.: US 9,265,875 B2
(45) Date of Patent: Feb. 23, 2016

(54) METHODS FOR TREATING BLOOD COMPOSITION AND FUNCTION DISORDERS WHEREIN A PATIENT'S BLOOD PLASMA IS EXTRACORPOREALLY CONTACTED WITH DONOR BLOOD OR MODIFIED DONOR BLOOD

(75) Inventor: Steffen Mitzner, Rostock (DE)

(73) Assignee: Artcline GmbH, Rostock (DE)

( * ) Notice: Subject to any disclaimer, the term of this patent is extended or adjusted under 35 U.S.C. 154(b) by 1069 days.

(21) Appl. No.: 12/918,425

(22) PCT Filed: Feb. 20, 2009

(86) PCT No.: PCT/EP2009/001233
§ 371 (c)(1),
(2), (4) Date: Nov. 12, 2010

(87) PCT Pub. No.: WO2009/103553
PCT Pub. Date: Aug. 27, 2009

(65) Prior Publication Data
US 2011/0042313 A1    Feb. 24, 2011

(30) Foreign Application Priority Data
Feb. 22, 2008   (DE) .................. 10 2008 010 691

(51) Int. Cl.
*A61M 1/34*   (2006.01)
*A61M 1/36*   (2006.01)
*B01D 37/00*  (2006.01)

(52) U.S. Cl.
CPC ............... *A61M 1/3633* (2013.01); *A61M 1/34* (2013.01)

(58) Field of Classification Search
USPC ......... 210/644, 645, 646, 647, 649, 650, 651, 210/652, 653, 634, 638, 765
See application file for complete search history.

(56) References Cited

U.S. PATENT DOCUMENTS

| | | | |
|---|---|---|---|
| 5,843,474 A * | 12/1998 | Williams | 424/450 |
| 6,509,147 B1 | 1/2003 | Altrichter | 424/93.7 |
| 6,858,146 B1 | 2/2005 | Myers | 210/645 |
| 2003/0129736 A1* | 7/2003 | Mitrani | 435/284.1 |
| 2003/0130194 A1* | 7/2003 | Altrichter et al. | 514/12 |

(Continued)

FOREIGN PATENT DOCUMENTS

| | | |
|---|---|---|
| DE | 19519065 | 11/1996 |
| DE | 19627685 | 1/1998 |

(Continued)

OTHER PUBLICATIONS

Wikipedia Reference, Accessed Sep. 5, 2013, PDF in file.*

(Continued)

*Primary Examiner* — Allison Fitzsimmons
(74) *Attorney, Agent, or Firm* — Smith Sambrell & Russell LLP

(57) ABSTRACT

The present invention relates to a method for treating blood composition disorders and blood function disorders. Said method comprises steps, in which blood or blood plasma of a patient is brought into extracorporeal contact with a second fluid (bioequivalent), wherein said second fluid is blood or modified blood, which comprises at least granulocytes, thrombocytes, and erythrocytes. Furthermore, the invention relates to devices for performing said method and to the use of such a device or blood or modified blood, which comprises granulocytes, thrombocytes, and erythrocytes, for treating blood composition disorders and blood function disorders.

12 Claims, 4 Drawing Sheets

(56) References Cited

U.S. PATENT DOCUMENTS

Figure 1:
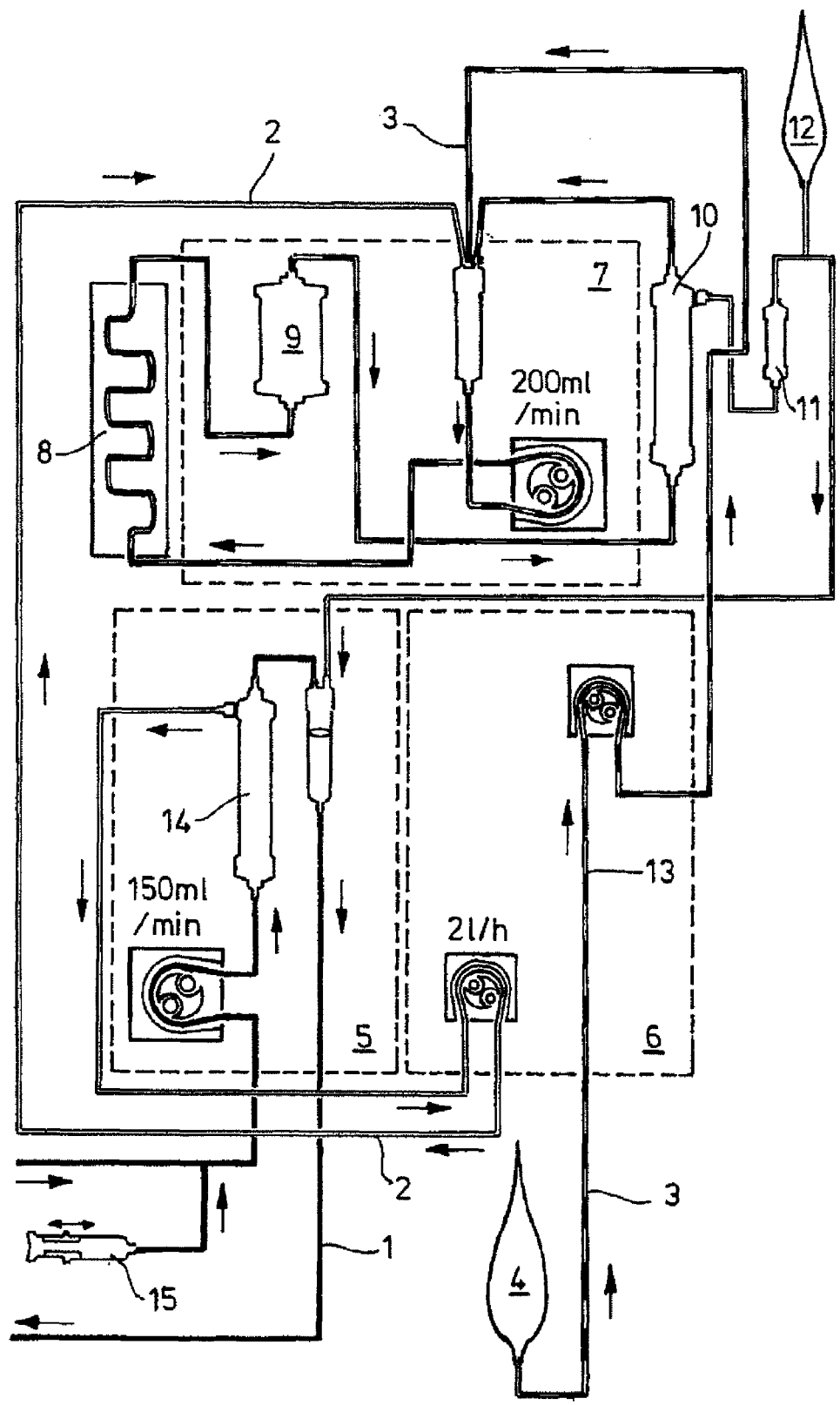

| | | | | |
|---|---|---|---|---|
| 2008/0145926 | A1 | 6/2008 | Kugelmann | 435/297.4 |
| 2011/0042313 | A1 | 2/2011 | Mitzner | 210/638 |
| 2013/0071350 | A1 | 3/2013 | Lentz | 604/4.01 |

FOREIGN PATENT DOCUMENTS

| | | |
|---|---|---|
| DE | 19831873 | 3/2000 |
| DE | 19854338 | 6/2000 |
| DE | 19916352 | 10/2000 |
| DE | 102005021305 | 11/2006 |
| DE | 202081010691 | 8/2009 |
| EP | 1731162 | 12/2006 |
| EP | 2254619 | 12/2010 |
| WO | WO 01/51068 | 7/2001 |
| WO | WO 2007/046757 | 4/2007 |
| WO | WO 2009/103553 | 8/2009 |

OTHER PUBLICATIONS

U.S. Appl. No. 10/181,291, filed Jul. 15, 2002, Jens Altrichter.

International Search Report issued Sep. 0909 for Application PCT/EP2009/001233 filed Feb. 20, 2009, which published as WO 2009/103553 on Aug. 27, 2009 (Universität Rostock // Steffen Mitzner) (2 pages).

Written Opinion issued Aug. 2, 2010 for Application PCT/EP2009/001233 filed Feb. 20, 2009, which published as WO 2009/103553 on Aug. 27, 2009 (Universität Rostock // Steffen Mitzner) (4 pages).

International Preliminary Report on Patentability issued Sep. 2, 2010 for Application PCT/EP2009/001233 filed Feb. 20, 2009, which published as WO 2009/103553 on Aug. 27, 2009 (Universität Rostock // Steffen Mitzner) (5 pages).

Allowed Claims for European Application No. 09712372.3 (now European Patent EP2254619 issued May 10, 2012) (Applicant—Universität Rostock // Inventor—Steffen Mitzner) (3 pages).

Allen JW, et al. Advances in bioartificial liver devices. Hepatology 34:447-455, 2001.

Ash Sr. Hemodiabsorption in treatment of acute hepatic failure and chronic cirrhosis with ascites. Artif Organs 18:355-362, 1994 (Abstract Only).

Bellomo R, et al. Extracorporeal blood treatment (EBT) methods in SIRS/Sepsis. Int J Artif Organs 28: 450-458, 2005.

Blessing F, et al. Heparin-mediated extracorporeal low-density lipoprotein precipitation: rationale for a specific adjuvant therapy in cardiovascular disease. Transfus Apher Sci. 30: 255-266, 2004.

Busund R, et al. Plasmapheresis in severe sepsis and septic shock: a prospective, randomized, controlled trial. Intensive Care Med. 28(10): 1434-1439, 2002.

Caille V, et al. Histocompatibility leukocyte antigen-D related expression is specifically altered and predicts mortality in septic shock but not in other causes of shock. Shock 22: 521-526, 2004.

Cole L, et al. A phase II randomized, controlled trial of continuous hemofiltration in sepsis. Crit Care Med. 30: 100-106, 2002.

Demetriou AA, et al. Prospective, randomized, multicenter, controlled trial of a bioartificial liver in treating acute liver failure. Ann Surg 239:660-667, 2004.

Docke WD, et al. Monocyte deactivation in septic patients: restoration by IFN-gamma treatment. Nat Med. 3(6): 678-681, 1997.

Humes HD, et al. Initial clinical results of the bioartificial kidney containing human cells in ICU patients with acute renal failure. Kidney Int. 66:1578-1588, 2004.

Kaufmann I, et al. Polymorphonuclear leukocyte dysfunction syndrome in patients with increasing sepsis severity. Shock 26: 254-261, 2006.

Konstantin P, et al. Artificial liver. Artif Organs 16: 235-242, 1992.

Lehmann HC, et al. Plasma exchange in neuroimmunological disorders: part 2. Treatment of neuromuscular disorders. Arch Neurol. 63: 1066-1071, 2006.

Mitzner SR. Albumin dialysis: an update. Curr Opin Nephrol Hypertens. 16: 589-595, 2006.

Oberholzer A, et al. Sepsis syndromes: understanding the role of innate and acquired immunity. Shock. 16: 83-96, 2001.

O'Grady JG, et al. Controlled trials of charcoal hemoperfusion and prognostic factors in fulminant hepatic failure. Gastroenterol 94:1186-1192, 1988.

Opolon P, et al. Hepatic failure coma (HFC) treated by polyacrylonitrile membrane (PAN) hemodialysis (HD). Trans Am Soc Artif Intern Organs 22:701-708, 1976.

Ploder M, et al. Lipopolysaccharide-induced tumor necrosis factor alpha production and not monocyte human leukocyte antigen-DR expression is correlated with survival in septic trauma patients. Shock 25: 129-134, 2006.

Ronco C, et al. The role of extracorporeal therapies in sepsis. J Nephrol. 16 Suppl 7: S34-S41, 2003.

Ronco C, et al. A pilot study of coupled plasma filtration with adsorption in septic shock. Crit Care Med. 30(6): 1250-1255, 2002.

Safdar A, et al. Impact of high-dose granulocyte transfusions in patients with cancer with candidemia: retrospective case-control analysis of 491 episodes of *Candida* species bloodstream infections. Cancer 101: 2859-2865, 2004.

Stanworth SJ, et al. Granulocyte transfusions for treating infections in patients with neutropenia or neutrophil dysfunction. Cochrane Database Syst Rev. Issue 3, Article No. CD005339, 2005 (34 pages).

Stegmayr BG, et al. Plasma exchange as rescue therapy in multiple organ failure including acute renal failure. Crit Care Med 31(6): 1730-1736, 2003.

Tetta C, et al. Artificial organ treatment for multiple organ failure, acute renal failure, and sepsis: recent new trends. Artif Organs 27(3): 202-213, 2003.

Vale JA, et al. Use of charcoal haemoperfusion in the management of severely poisoned patients. Br Med J 1(5948): 5-9, 1975.

van de Kerkhove MP, et al. Clinical application of bioartificial liver support systems. Ann Surg. 240: 216-230, 2004.

Weston MJ, et al. Effects of haemoperfusion through charcoal or XAD-2 resin on an animal model of fulminant liver failure. Gut 15: 482-486, 1974.

\* cited by examiner

METHODS FOR TREATING BLOOD COMPOSITION AND FUNCTION DISORDERS WHEREIN A PATIENT'S BLOOD PLASMA IS EXTRACORPOREALLY CONTACTED WITH DONOR BLOOD OR MODIFIED DONOR BLOOD

CROSS REFERENCE TO RELATED APPLICATIONS

The present application is a National Phase Application of International Application No. PCT/EP2009/001233, filed Feb. 20, 2009, which claims priority to German Patent Application No. 10 2008 010 691.7, filed Feb. 22, 2008, which applications are incorporated herein fully by this reference.

The present invention relates to a method for treating blood composition disorders and blood function disorders. This method comprises steps wherein blood or blood plasma of a patient is contacted extracorporeally with a second liquid (bioequivalent), wherein the second liquid is blood or modified blood which comprises at least granulocytes, thrombocytes, and erythrocytes. The invention further relates to apparatuses for carrying out this method and to the use of such an apparatus or of blood or modified blood which comprises granulocytes, thrombocytes, and erythrocytes for treating blood composition disorders and blood function disorders.

Blood is a complex organ which comprises many different cellular components and plasma components which interact with one another and with other endogenous systems. Cellular components include not only the erythrocytes but also leukocytes, inter alia, lymphocytes (B and T lymphocytes, NK cells, NK/T cells), thrombocytes, granulocytes (also referred to as polymorphonuclear leukocytes: neutrophils, eosinophils, basophils), monocytes/macrophages, dendritic cells, mast cells, and their precursors (e.g., hematopoietic stem cells). Plasma components include, for example, the complement system, coagulation factors, messengers, such as cytokines and hormones, and salts. The composition of blood of healthy individuals is described in, for example, "Labor and Diagnose" ("Laboratory and Diagnosis") (Thomas 2000).

Many diseases are associated with, in some cases, complex changes in the blood composition, whereby pathophysiologically relevant processes are initiated or sustained. Corrective approaches using medicaments often remain limited to the neutralization or normalization of individual factors and can therefore often not achieve the desired clinical normalization effect. The same applies to the transfusion of whole blood or blood constituents, and also to conventional extracorporeal blood treatment methods, which generally achieve only a crude change in the composition of the blood, such as, for instance, the removal of a total fraction of the blood, with the loss not only of substances whose removal is desired (e.g., toxins) but also of valuable substances (e.g., during plasma exchange). Other extracorporeal methods, on the other hand, aim for selective removal of individual harmful substances and therefore have only a selective effect (e.g., specific adsorption).

Medicamentous Therapies

Medicamentous therapy approaches represent an important aspect of modern medicine. In the majority of cases, the medicament has a systemic effect. The systemically acting agents affect the blood insofar as that the medicamentous effect is generally mediated via the blood and the blood composition and/or blood function are affected. This effect is often selective, i.e., a medicament remedies a singular problem, for instance, in the offsetting of deficiencies (electrolyte administration in the case of electrolyte deficiency, glucose administration in the case of glucose deficiency, hormone substitution in the case of a corresponding deficiency, etc.), or triggers a mechanism which helps to counterregulate a pathophysiological problem (e.g., anticoagulation in the case of hypercoagulability and vessel wall damage, immunosuppression in the case of autoimmune processes, administration of neutralizing antibodies in the case of immune dysfunctions).

A further application area of medicamentous therapies is the—more or less selective—killing of harmful endogenous cells (chemotherapy in the case of tumors) or foreign organisms (administration of antibiotics in the case of infections). The blood composition and blood function can also be changed by blood cell growth factors (erythropoietin, thrombopoietin, G-CSF, GM-CSF), in terms of cellular changes, and by vitamin K administration, in terms of plasma changes.

However, these selective therapies often cannot achieve the desired goal alone, but also require, for example, the involvement of endogenous systems. Also the use of neutralizing antibodies, for example, anti-LPS, anti-TNF alpha, etc., with the aim of correcting pathological concentrations of toxin or messenger is often not sufficient for curing a disease. A further disadvantage of the medicamentous therapies are the adverse drug reactions which can, in some cases, be serious and can, in the worst case, worsen the disease progression or even lead to the death of the patient (e.g., allergic and toxic reactions, opportunistic infections following chemotherapy or immunosuppression, undesired effects of the activation of immune cells).

Transfusions of Blood/Blood Cells/Plasma

Blood transfusions and plasma transfusions are a standard therapy in modern medicine. They are used specifically for offsetting deficiencies in the patient's blood (inter alia, cytopenias, low volume, coagulation factor deficiency). In addition to whole blood transfusions, especially concentrates of the individual blood cell types are used (erythrocyte concentrates, thrombocyte concentrates, granulocyte concentrates). While erythrocytes and thrombocytes are administered in the case of anemia and thrombopenia with the risk of bleeding, respectively, the area of use of granulocyte donations is in granulocyte deficiency (in extreme cases, agranulocytosis) for treating neutropenic infections. By introducing steroid-induced or G-CSF-induced granulocyte concentrates having a high cell number, the clinical results in granulocyte transfusion were improved (Stanworth 2005, Safdar 2004).

Methods for treating a hepatic coma are known in which the blood of the patient is completely washed out of the body of the patient and replaced with Ringer's lactate solution, supplemented to some extent with albumin (total body washout), and the circulation is subsequently filled again with normal blood. Methods in which the blood of a patient is completely replaced by means of blood transfusion have been used for a long time.

The advantages are removal of toxins from the circulation and the supply of fresh/healthy cells and plasma components, such as coagulation factors. Direct transfusion from donor to recipient would lead to the best results, but is not practical, since various compatible donors would have to be present for each treatment. Therefore, use has to be made of citrate- or heparin-treated blood, which can lead to acidosis, hyperkalemia, a high citrate level, and hyperammonemia, and also to disturbances of the acid-base balance in the blood. In subsequent liver failure studies, a poor survival rate was observed. Extrahepatic complications associated with the method include aspiration, bleedings, hypoglycemia, sepsis, bronchospasms, and brain edema, often resulting in death.

Granulocyte transfusions (GTx), more particularly at a high dose, led, in some cases, to an improvement in the survival rate of patients with neutropenia, a neutronphilic dysfunction, with cancer-associated infections or sepsis (Safdar 2004, Stanworth 2005). Allogeneic blood transfusions, however, increase the risk of multiple organ failure. The transfusion of leukocytes also brings with it an immunosuppressive potential which can worsen the clinical situation of sepsis patients (Moore 1997, Gianotti 1993).

Extracorporeal Methods

Extracorporeal treatment methods include dialysis/filtration, plasma exchange/plasma perfusion/plasma adsorption, bioreactor therapies, and extracorporeal organ perfusion.

An overview of extracorporeal blood treatment methods for different indications can be found in the following publications: *Acute Kidney Failure and Blood Poisonings* (Ronco 1998), *Liver Failure* (van de Kerkhove 2004, Mitzner 2007), *Neurological Autoimmune Diseases* (Lehmann 2006), *Lipometabolism Diseases* (Blessing 2004), *Sepsis* (Bellomo 2005).

Extracorporeal blood detoxification methods can decisively affect the clinical progression of, for example, sepsis and multiple organ failure (Ronco 2003). Hemofiltration, hemodialysis, plasma perfusion or whole blood perfusion through adsorbing columns (e.g., activated carbon, immobilized polymyxin B, or DEAE) were used in this context (Bellomo 2005). Cytokines can be removed to a substantial extent from the circulation of septic patients by means of hemofiltration/plasma filtration, but this did not necessarily lead to a significant increase in the survival rate in some studies (Cole 2002). Larger controlled studies are still missing; however, the existing data indicate that those methods which can remove larger molecules/particles from plasma (e.g., treatment with large volumes, filtration with large pores, plasmapheresis and adsorption) have a greater effect on the disease progression than those methods which in particular affect smaller, water-soluble molecules (Busund 2002, Stegmayr 2003, Ronco 2002, Tetta 2003).

It has been shown that hemoperfusion via activated carbon has positive effects in the case of external poisoning (Vale 1975). The method has been used since 1972 with variable success for hepatic coma due to various causes (O'Grady 1988). Ion-exchange resins can bind protein-bound substances in particular and are therefore likewise used for, for example, treating liver failure (Weston 1974).

The most important disadvantages of hemoperfusion are the lack of selectivity, since an adsorption of hormones, vitamins, immunoglobulins, medicaments, and other plasma components also occurs, as well as an activation of the complement cascade, thrombocytopenia, and leukocyte marginalization.

Hemodialysis, in particular with large-pored membranes, the high flow-rate membrane AN69 (polyacrylonitrile, PAN) for example, and with a closed dialysate circuit with sterile acetate-buffered dialysate, was likewise used for treating liver failure (Opolon 1976, Konstantin 1992). In this method, medium-sized molecules having a molecular weight of up to 5000 daltons can also be removed, but not hydrophobic and/or protein-bound substances, such as short-chain or medium-chain fatty acids, mercaptans, or bilirubin.

Hemodiabsorption is a process in which blood flows through packages of dialysis membranes surrounded by a suspension of fine absorbing particles, and thus essentially represents a combination of a sieving method (dialysis) and absorption. For example, use was made (Ash 1994) of a dialysis system having an absorbing suspension, in which a dialysis instrument having a flat cellulose membrane was perfused on one side with the blood of the patient and on the other side with a dialysate of a mixture of activated carbon and anion-exchange-resin particles.

Dialysis systems having hollow-fiber membranes and 20% human serum albumin as a molecular adsorption agent (molecular adsorbent recirculating system, MARS) (Mitzner 2007) are likewise known for treating blood composition disorders, such as in the case of liver failure.

In therapeutic plasma exchange (TPE), the blood of the patient is either centrifuged or filtered in order to separate the blood cells from the plasma. The plasma of the patient is then replaced by the plasma of healthy donors, normally fresh frozen plasma (FFP), and this plasma is transfused with the blood cells into the patient. FFP is more easily obtainable and manageable than whole blood, providing an advantage compared with the exchange of total blood. An overview is given in (Bambauer 1988). There is, however, a high complication rate, in particular bacterial infections, pulmonary edema, and bleedings. The use of citrate plasma results in hypocalcemic cramps despite additional dialysis and replacement of calcium.

The therapeutic use of extracorporeal bioreactors already has a long tradition. Concepts based on cell-based extracorporeal organ support have been successfully used in acute liver failure (Allen 2001, Demetriou 2004) and acute kidney failure associated with sepsis (Humes 2004).

In the prior art, an extracorporeal plasma perfusion is proposed, with use of a bioreactor with immunomodulatory cells (such as endothelial cells, leukocytes, cells derived by differentiation from hematopoietic stem cells or cell lines of these cell types) which can adsorb immunomodulatory substances via receptors or can release such substances (DE 198 31 873, WO 01/51068). Also, an extracorporeal plasma perfusion of a bioreactor with phagocytes, such as granulocytes or monocytes/macrophages, is proposed, in which functions of the granulocytes are to be used in order to clean the plasma of the patient of harmful substances and pathogens by means of phagocytosis. Supplementing the cells in the bioreactor with other individual cells, such as hepatocytes or endothelial cells, is mentioned. It is proposed, for example, to use cell lines or cells differentiated from hematopoietic stem cells.

In light of this, the problem facing a person skilled in the art is to provide a therapy method or therapy system which can analyze the current situation of a patient by means of a biosensor and can simultaneously, in a regulatory manner, change the blood composition, not only on an individual basis and specifically, but also comprehensively and in a complex way.

The problem is resolved by the subject matter of the claims. More particularly, a method for treating blood composition disorders and blood function disorders is provided, which comprises steps wherein blood or blood plasma of a patient is contacted extracorporeally with a second liquid (bioequivalent), where the second liquid is blood or modified blood which comprises granulocytes, thrombocytes, and erythrocytes.

More particularly, the bioequivalent comprises at least $0.4 \times 10^{10}$ leukocytes per L, more particularly $1\text{-}200 \times 10^{10}$ leukocytes per L, comprising at least $0.2 \times 10^{10}$ granulocytes per L, at least $1.0 \times 10^9$ thrombocytes per L, and at least $1.0 \times 10^9$ erythrocytes per L.

Preferably, the bioequivalent in particular comprises $1\text{-}100 \times 10^{10}$ granulocytes per L, preferably at least $1.5 \times 10^{10}$ granulocytes per L or at least $3 \times 10^{10}$ granulocytes per L. Preferably, the bioequivalent comprises $1.0 \times 10^9\text{-}5 \times 10^{11}$ thrombocytes per L, in particular at least $5 \times 10^9$ or at least $1 \times 10^{10}$ thrombocytes per L. In a preferred embodiment, the bioequivalent comprises at least $1.0 \times 10^9$ erythrocytes per L, more particularly $5.0 \times 10^9$-$8.0 \times 10^{12}$ erythrocytes per L or $0.1$-$8.0 \times 10^{12}$ erythrocytes per L, but typically $0.5$-$6.0 \times 10^{12}$ erythrocytes per L. Such values are also achieved with a fairly strong depletion of erythrocytes because of the high number of erythrocytes in blood.

It was found in the context of the invention that, surprisingly, the use of blood or modified blood which in particular comprises the granulocyte and thrombocyte cell types at a high concentration has a positive effect on the clinical result. The use of modified blood instead of individual cell types, as in the prior art, ensures that the bioequivalent is capable of providing all essential organ functions of healthy blood for treating composition disorders and/or function disorders of the patient's blood.

Accordingly, it is particularly preferred that the bioequivalent also comprises significant amounts of lymphocytes and/or monocytes (monocytes/macrophages). All cell types which are found in healthy blood should be represented; the concentrations can, however, deviate from the normal concentrations in blood. In a preferred embodiment, the bioequivalent comprises at least $0.4 \times 10^{10}$, more preferably $2.0 \times 10^{10}$, lymphocytes per 1 and more particularly at least $1.0 \times 10^8$ lymphocytes per 1. In a preferred embodiment, the bioequivalent comprises at least $1.0 \times 10^8$ monocytes per 1.

Preferably, a volume of bioequivalent of about 100 mL to about 20 L, in particular about 200 mL, about 500 mL, about 1 L, about 2 L, or about 5 L, is used.

In one embodiment of the invention, the bioequivalent further comprises blood plasma. This plasma can contribute essential factors for treating function disorders and composition disorders, for example, by supplementing missing plasma factors of the patient's blood. A diluting out of important plasma factors of the patient's blood is also prevented. Alternatively, the blood plasma in the modified blood can be partially or completely replaced by physiological saline solution or a biocompatible buffer. For example, the selective depletion of individual plasma factors may make sense in certain disease situations. This will depend on the situation of the patient and possible incompatibilities of donor's blood and patient's blood.

Bioequivalent, in the context of the invention, refers to a healthy donor's blood or modified blood which, in the context of an extracorporeal treatment of blood or blood plasma of a patient, can take over and/or supplement organ functions of this patient, for the purpose of a temporary auxiliary organ transplantation. The bioequivalent provided by the invention retains essential properties arising as a result of the complexity of whole blood as an organ and is functionally identical—partially or completely—to whole blood. In particular, the bioequivalent is intended to enable biospecific adsorption or neutralization similar to that of whole blood. A modification of the whole blood should affect this property as little as possible, preferably not at all. The modification preferably enhances favorable, desired properties (e.g., by increasing the state of activity or the concentration of individual plasma constituents or cell types); unfavorable, undesired properties are attenuated (e.g., by depleting individual plasma constituents or cell types, volume modification). Whole blood itself is a bioequivalent for the purpose of this definition, in which the degree of modification is nil. A typical source of bioequivalents are human blood donors. The modification can be achieved by, inter alia, additives, passage over adsorbents, filtration processes and separation processes, and also physical or chemical processing.

The bioequivalent can comprise blood which is modified by, for example, volume restriction (e.g., by partial plasma withdrawal), leukocyte fraction enrichment (e.g., by suitable centrifugation steps), leukocyte depletion (or depletion of individual leukocyte types, for example, of B lymphocytes), erythrocyte depletion, depletion of antibodies, irradiation, coagulation inhibition, and/or stabilization.

A depletion of antibodies can, for example, be advantageous in the prevention of secondary effects, such as transfusion-associated lung failure. It can, for example, be achieved via adsorption of antibodies to a Protein A or Protein G column.

In order to simplify storage of the blood, stabilizers (e.g., buffers or cell nutrient solutions) and coagulation-inhibiting substances (e.g., citrate-based solutions, such as, ACD solution (acid-citrate-dextrose, a solution of citric acid, sodium citrate, and D-glucose in water) can be added. To treat some conditions, in the case of sepsis for example, it may also be advantageous to condition the modified blood, i.e., to prestimulate with LPS for example.

Preferably, there is an enrichment of granulocytes and thrombocytes in the modified blood. The bioequivalent is, for example, obtainable by plasmapheresis, wherein, for example, the formation of granulocytes may have been promoted by prior administration of stimulants, such as G-CSF or steroids. The modified blood can be a granulocyte concentrate or a buffy coat. Methods for acquiring a granulocyte concentrate or a buffy coat are known in the prior art.

The blood or modified blood used in the context of the invention is preferably chosen (e.g., blood group match) and/or monitored according to the criteria for a blood transfusion. The donor should be healthy. Blood donations are usually tested for the presence of disease pathogens, and this should also be applied here. Normally, the method is applied to humans, i.e., both the patient and the recipient are human; however, use in animals is also possible in principle.

The use of healthy whole blood or a suitable bioequivalent extract thereof (bioequivalent) in an extracorporeal system communicating with the patient's blood or blood plasma for treating blood function disorders and blood composition disorders enlarges the effective blood volume or plasma volume of the patient to such an extent that circulating toxins are (a) diluted out below a critical limit or (b) biospecifically adsorbed/neutralized in the bioequivalent. The bioequivalent can furthermore (c) react to harmful stimuli as an entire organ, actively, comprehensively, and in a complex way. A complex biocommunication between whole blood/bioequivalent, on the one side, and patient's blood, on the other side, takes place. In the context of this biochemical information exchange, (I) the bioequivalent "learns" about the disease state of the patient and (II) the bioequivalent overcomes the lack of communication or controls the miscommunication in the patient's blood. A normalization even of complex harmful substance patterns or suitable bioprocessing takes place, leading to an environment which enables organ-regenerative processes, and in which the status of health of the patient stabilizes.

Complex biocommunication is understood to mean the entirety of the biochemical, physical, and other signal exchange taking place in and with the bioequivalent. This includes cell-to-cell communication (by direct contact, e.g., via receptors, and indirectly via messengers), cell-to-plasma communication, and plasma-to-plasma communication. Disturbances of the composition of the bioequivalent by contact with the blood or plasma of the patient will generally lead to a modified complex biocommunication. This may initiate targeted responses and processes which lead to a counterregulation.

In the method according to the invention, the cells of the bioequivalent are not intended to be supplied to the body of the patient. In one embodiment, this can be achieved by carrying out the method according to the invention in a way that it comprises steps in which a) blood plasma acquired from patient's blood (simultaneous to its acquisition or at a later time) is fed to the bioequivalent,
b) by means of a filtration step, the modified blood plasma is separated from the cells of the bioequivalent so that it can be supplied to the patient's blood again.

The blood plasma can be acquired from patient's blood by, for example, setting up a pressure gradient over a semipermeable membrane. An acquisition is also possible via centrifugation or plasmapheresis. Useful methods and apparatuses are known in the prior art. The preferred variant is membrane plasma separation using a single-use hollow-fiber plasma separator (e.g., using the BM25 instrument from Baxter/Edwards and a PF 1000 membrane plasma filter from Gambro AB, Lund).

In another embodiment of the invention, patient's blood or patient's blood plasma is contacted with the bioequivalent, wherein the patient's blood or patient's blood plasma and the bioequivalent are separated from one another by a semipermeable membrane permeable to plasma.

Preferably, the exclusion limit of the membrane pores of a semipermeable membrane used in the context of the invention and permeable to plasma but not permeable to cells is between a minimum of about 5000 daltons and a maximum of an average pore diameter of about 0.8 µm. The membrane properties (average pore size, polymer materials, membrane architecture) can be used for a regulatory effect on the transmembranal substance exchange and transmembranal information exchange. A typical membrane has an average pore diameter of about 0.2 µm.

The membrane can, for example, be a hollow-fiber membrane or a flat membrane. The membrane can be a membrane coated on one or both sides or uncoated. Materials of which the membrane can consist of are, for example, polycarbonate, PE, PTFE, polypropylene, or nylon. A preferred membrane plasma separator consists of, for example, polypropylene hollow fibers and has an effective membrane surface area on the blood side in the range from 0.1 to 0.5 $m^2$.

Since blood or a bioequivalent is used on the dialysate side in the system according to the invention—in contrast to conventional dialysis systems—it is preferred that the membrane is biocompatible at least on this side (i.e., is not toxic for the blood cells present there or does not activate these cells); preferably, it is biocompatible on both sides. Coatings of the membrane can contribute here, for example, coatings of biologically active substances (such as coagulation inhibitors, proteins) or of biologically inert substances (such as metals or ceramic materials).

Since the cells of the bioequivalent are not administered to the patient, irradiation of these cells, while being possible, is not absolutely necessary.

Preferably, the patient's blood or patient's blood plasma is moved directionally in an extracorporeal circulation and/or the bioequivalent is moved directionally. Both a contrary and a noncontrary movement are possible, i.e., the two liquids are conducted either in opposed directions along the separation membrane (countercurrent flow), or in a parallel flow. Under all conditions, it should be ensured that the patient's blood or patient's blood plasma is contacted under suitable conditions (similar to those for a cell culture) and for a suitable time to achieve the improvement of the blood function disorders and blood composition disorders after administration of the treated patient's blood/patient's blood plasma.

It should be noted that the method according to the invention can be carried out when the patient's blood or patient's blood plasma in an extracorporeal circulation is connected with the circulation of the patient or is separated from this circulation, for instance, after acquisition of the patient's blood plasma, for example, by means of plasmapheresis, incubation of the plasma with the bioequivalent, separation of at least the cell components of the bioequivalent prior to infusion with the patient.

The embodiment of the invention wherein the patient's blood or patient's blood plasma and the bioequivalent are separated from one another by a semipermeable, plasma-permeable membrane solves the problem of contacting patient's blood with the bioequivalent in such a way that, on one hand, a complex biocommunication between healthy and diseased blood becomes possible and, on the other hand, a control of the exchange and, preferably as well, a complete separation of the systems at any time can be accomplished, wherein this can be achieved in a volume-balance-neutral manner, i.e., without disturbing the volume homeostasis of the patient.

At the same time, the membrane represents a safety barrier for the patient (for instance, against cell-mediated allergic reactions, infections, cell crossover with subsequent induction of organ damage, e.g., acute lung damage, etc.).

Bioequivalence space, in the context of the invention, refers to the extracorporeally situated space in which the bioequivalent is present during the treatment. The bioequivalence space is, in one embodiment, separated from the patient's blood by a semipermeable membrane. Through the membrane, the patient's blood (plasma) and bioequivalent communicate with one another. The connection of bioequivalence space and patient's blood (plasma) is reversible and can be disengaged at any time.

As a result, the following potentially undesired results of the communication can preferably be regulated/prevented:
a) development or intensification of unfavorable properties of the bioequivalent potentially harmful to the patient,
b) cell debris influx from the bioequivalence space into the patient,
c) influx of harmful cell products/plasma components into the patient,
d) loss of useful cell products/plasma components from the patient,
e) hemodynamic instability of the patient through volume losses.

In order to be able to externally influence these parameters, it is helpful when the status of the bioequivalent and/or of the patient's blood/patient's blood plasma is monitored, for example, by means of chemical or physical methods. This can be carried out continuously and makes sense for all embodiments of the invention.

The method according to the invention is, in one embodiment, an extracorporeal blood treatment method which can be operated at the patient's bedside for correcting complex harmful substance patterns by
a) depleting harmful substances/reducing the influence of harmful principles by means of dilution and/or
b) biospecific adsorption/neutralization in the bioequivalence space and/or
c) bioactive counterregulation mediated by the bioequivalent
d) complex biosensory online analysis between the patient's blood and the therapeutic bioequivalent
e) transmembrane control of complex biocommunication in a membrane-separated two-compartment system (extracorporeal blood circulation and bioequivalence space.

The method according to the invention is also referred to as bioequivalence dialysis (BED), disequilibrium whole blood dialysis (DVD), or biosystem dialysis (BSD).

In the context of the present invention, a blood composition disorder or blood function disorder can be, for example, sepsis or septic shock, in particular in the phase of immunoparalysis, renal insufficiency, liver insufficiency, immunodeficiency, or an infectious disease, or be associated with it.

One area of use of the method according to the invention is thus, for example, sepsis therapy. In advanced stages of sepsis (severe sepsis and septic shock), a complex disorder of blood composition and blood function is present. A central element of this disorder is immunoparalysis (also known as compensatory antiinflammatory response syndrome, CARS) (Oberholzer 2001). It was shown that functional impairment of the neutrophils or monocytes as central components of the innate immune system is clearly associated with an increased mortality in advanced stages of sepsis and septic shock (Docke 1997, Caille 2004, Ploder 2006, Kaufmann 2006).

In the context of the present invention, an apparatus for carrying out the method according to the invention is also provided, comprising two spaces separated by one or more semipermeable membrane(s), wherein one space is suitable for accepting patient's blood or blood plasma, and the second space is suitable for accepting the bioequivalent. This suitability in particular is a result of the membrane, which, as portrayed above, is biocompatible, especially (also) the membrane side which is in contact with the bioequivalent. In one embodiment of the invention, the apparatus is a conventional dialysis apparatus which is equipped with a semipermeable membrane which is biocompatible at least on the side which is in contact with the bioequivalent. The apparatus may already comprise bioequivalent in the second space (the bioequivalence space). The apparatus preferably is an apparatus such as that shown in FIG. 1, and comprises the constituents illustrated schematically therein. In particular, the apparatus according to the invention may comprise a MARS monitor (Gambro AB) and a BM11 and BM14 instrument each (Baxter/Edwards). In a particular embodiment, the volume of the second space is variable; it preferably is in the range from 100 mL to 20 L.

The invention also teaches the use of an apparatus according to the invention for treating a blood composition disorder or blood function disorder.

The invention further relates to the use of blood or a liquid acquired from it, which comprises granulocytes, thrombocytes, and erythrocytes and whose preferred configurations are described above (bioequivalent), for treating a blood composition disorder or blood function disorder, or for producing a medicament or medical product for treating a blood composition disorder or blood function disorder. With this treatment, blood or blood plasma of a patient is, as described above, contacted extracorporeally with the bioequivalent.

In the context of the present invention, it is described for the first time how an effective enlarging of the blood organ space is performed without having to accept possible secondary effects, such as allergies or cell-mediated infections and tissue damage. For the first time, the function of the blood as a complex liquid organ is used therapeutically, extracorporeally, and reversibly. A smoothing of complex pathological patterns of states in the patient's blood is achieved. Medically, the advantage lies in a qualitatively and quantitatively novel dimension of changing the state of a patient's blood, which dimension becomes clinically noticeable through better clinical results compared with the conventional prior art.

The teachings according to the invention also differ from the prior art in that it does not proceed inductively but deductively. This means that no individual components of the solution are defined for individual problems, or no arbitrarily constructed combination of individual components is meant to lead to a systemic solution (such as, for example, in liver cell bioreactors or the system proposed in the applications DE 195 19065, DE 198 31 873, or WO 01/51068); instead, a complete biosystem (blood), which is generally known and biologically defined as a functional unit, is used either in an unchanged manner or changed from a general form (normal whole blood) to a particular form. "Changed to a particular form" is intended to be understood to mean that whole blood is prepared for the specific requirements of the subsequent treatment, such as portrayed above.

Hereinafter, the invention will be illustrated by means of examples which are, however, not intended to be understood as limiting.

EXAMPLE

Ten intensive-care-unit patients with septic shock were each treated twice with the method according to the invention. After the identification of suitable patients, a blood donor of the same blood group as the respective patient was invited to donate by the transfusion medicine department of the hospital. After prestimulation of the donor with methylprednisolone, the withdrawal of the donor cells was carried out on the following day (density gradient centrifugation with hydroxyethyl starch (HAES)/citrate according to the standard protocol for granulocyte donation in transfusion medicine). The twenty cell donations thus obtained, which contained from 1.4 to $3.4 \times 10^{10}$ granulocytes per liter, from 1.5 to $4.5 \times 10^{12}$ erythrocytes per liter, and from 1.3 to $7.1 \times 10^{11}$ thrombocytes per liter, i.e., the bioequivalent, were irradiated, and, immediately afterwards, the treatment was carried out at the patient's bedside for six hours.

For this purpose, the cells were given into a bioreactor system in which the cells were able to circulate through a system of tubes and vessel (driven by a peristaltic pump) (FIG. 1). In a second section of the apparatus, blood of the sepsis patient was led through a plasma filter, whereby a portion of the blood plasma was separated from the blood flow (plasma separation). This separated plasma was added online to the circulating bioequivalent. In the same volume per time ratio, plasma is removed from the bioequivalent by plasma separation (by means of a second plasma filter), and supplied to the patient's blood again. To avoid blood coagulation in the extracorporeal system, anticoagulation with heparin was carried out. The blood/plasma/bioequivalent present in the bioreactor system was kept from excessive cooling by instrument heating (i.e., maintained at a temperature of about 34-37° C.). The patient's blood flowed at 150-200 mL/min; the plasma flow was about 20-35 mL/min; the bioequivalent circulated at 200 mL/min.

After six hours, the treatment was ended. The bioreactor system was discarded; the bioequivalent was likewise discarded or used for laboratory analysis. The second treatment took place after one day (i.e., two treatments within 72 hours) and was carried out analogously to the first treatment.

Figure 2:
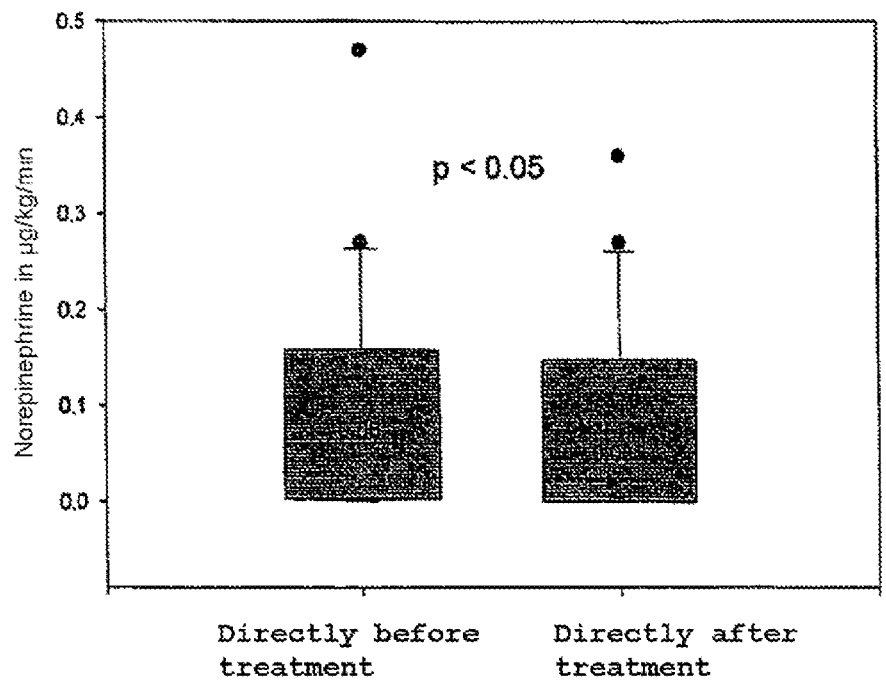

All patients tolerated the treatments well. Surprisingly, the circulation-shock situation of the patients improved even during the treatment, such that it was possible significantly to reduce the medicamentous circulation support with catecholamines (FIG. 2).

Figure 3:
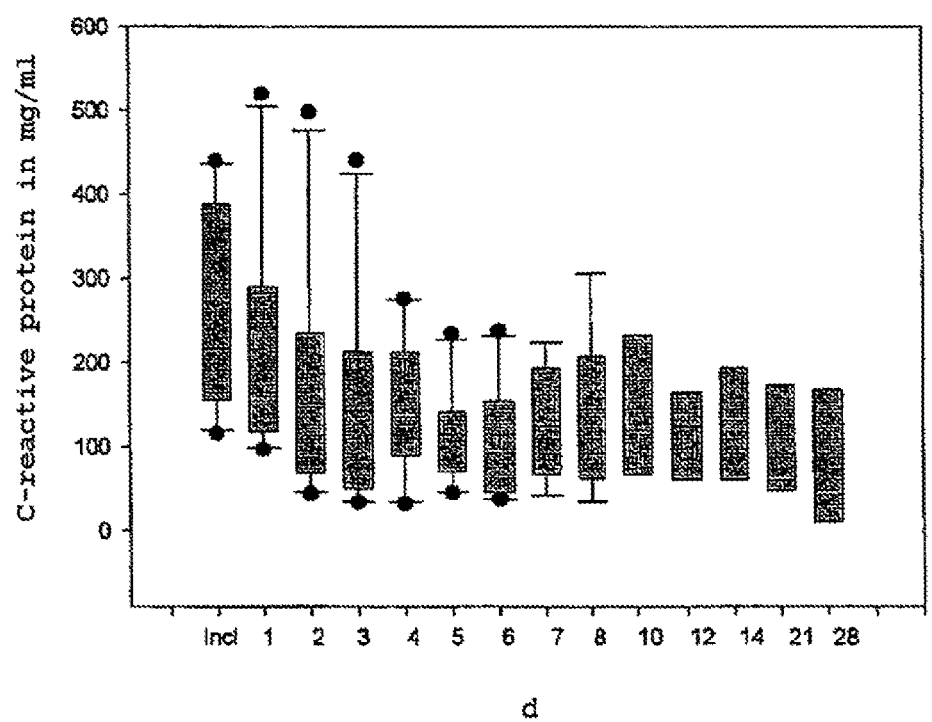
Figure 4:
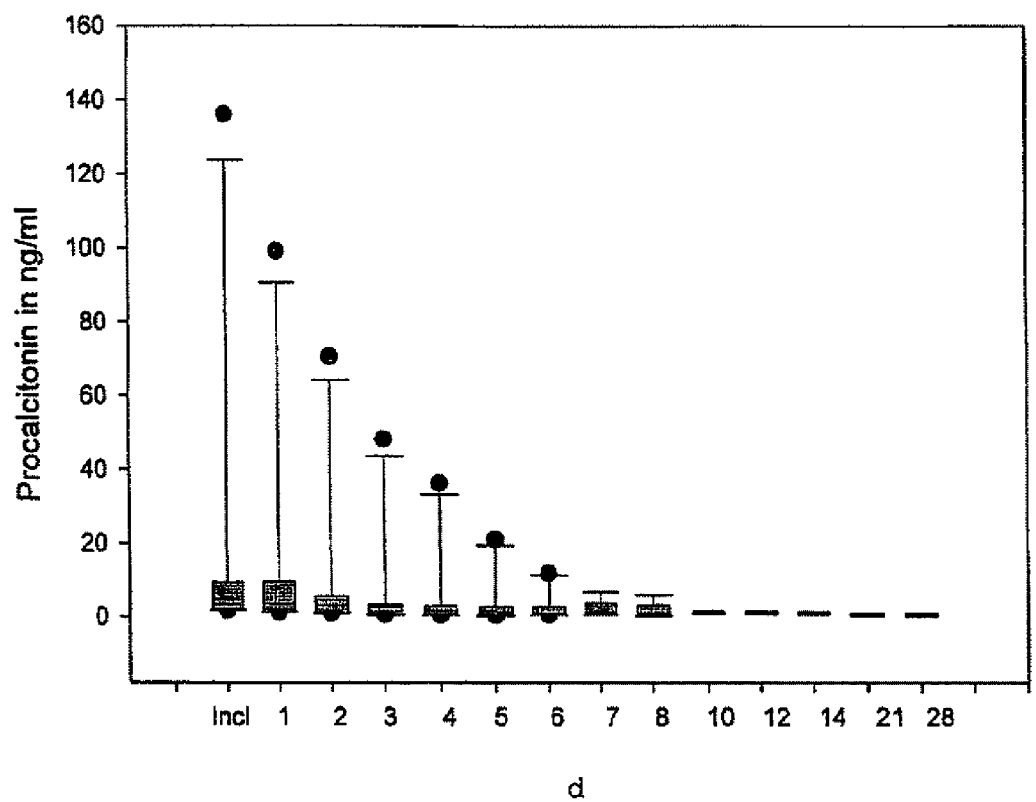

During the course of the following 28 days, the septic shock and multiorgan-failure situation improved for most of the patients (declining inflammation markers, for example, for C-reactive protein, procalcitonin, see FIGS. 3 and 4). The cellular immunocompetence of the patients improved significantly (increase in the HLA-DR value per monocyte, FIG. 5). Finally, the number and severity of the associated organ failure decreased (declining organ-failure score, SOFA, FIG. 6).

The survival rates—compared with the scores predictive of survival—were surprisingly high: seven patients survived for at least 28 days, and it was possible to discharge six from the hospital. The Acute Physiology and Chronic Health Evaluation (APACHE) II score predicted only 2-3 hospital survivors.

FIGURE LEGENDS

FIG. 1: Schematic illustration of a preferred treatment apparatus according to the invention (depicted showing filling of the equipment). Dark line: extracorporeal blood circulation of the patient/blood tubing (1). Light line: plasma flow after plasma separation from the patient's blood or from the bioequivalent/plasma tubing (2). Dotted line: bioequivalence space/cell circulation tubing (3).

Cell bag (4) represents the source of the cells of the bioequivalent. This connection is severed during the treatment. BM11 (5) and BM14 (6) are instruments which are manufactured by Baxter/Edwards (see above), and these instruments are also sold together and referred to as BM25; the MARS monitor (7) is manufactured by Gambro, Rostock. In each case, other instruments can also be used, including, for example, cell centrifuges suitable for separating plasma from cells. The instruments take over both filtration and the role of monitoring, if appropriate, the pressure and/or temperature, and driving the circulation (e.g., via roller pumps). The temperature control can be accomplished via, for example, the heating unit of the MARS monitor (heating bag (8)). Cell module (9) refers to an expansion and sedimentation space for the cells. CellFilter I (10) and CellFilter II (11) preferably are hollow-fiber-membrane plasma filters which retain the cells of the bioequivalent. PF1000N (Gambro), for example, can be used. CellFilter II is not necessary, but is an, in principle, redundant filter unit which has the same structure as CellFilter I and which can be used for safety reasons. While the system is filled, the liquid present in the apparatus which is then replaced by the bioequivalent is collected in the waste bag (12). This connection is severed during the treatment. (13) Cell infusion tubing; (14) PF1000N; (15) heparin; priming solution: heparinized HF solution.

FIG. 2: Catecholamine demand in sepsis patients before and after the treatment according to the invention: significant drop in the norepinephrine demand at stable blood pressure.

FIG. 3: 28-day course of the C-reactive protein (CRP) value in ten patients with septic shock (from the day of the first treatment with the method according to the invention. d=days of the study). Significant decrease of highly pathological values toward normal values over the period shown.

FIG. 4: 28-day course of the procalcitonin (PCT) value in ten patients with septic shock (from the day of the first treatment with the method according to the invention). Significant decrease of pathological values to the normal range of values over the period shown.

Figure 5:
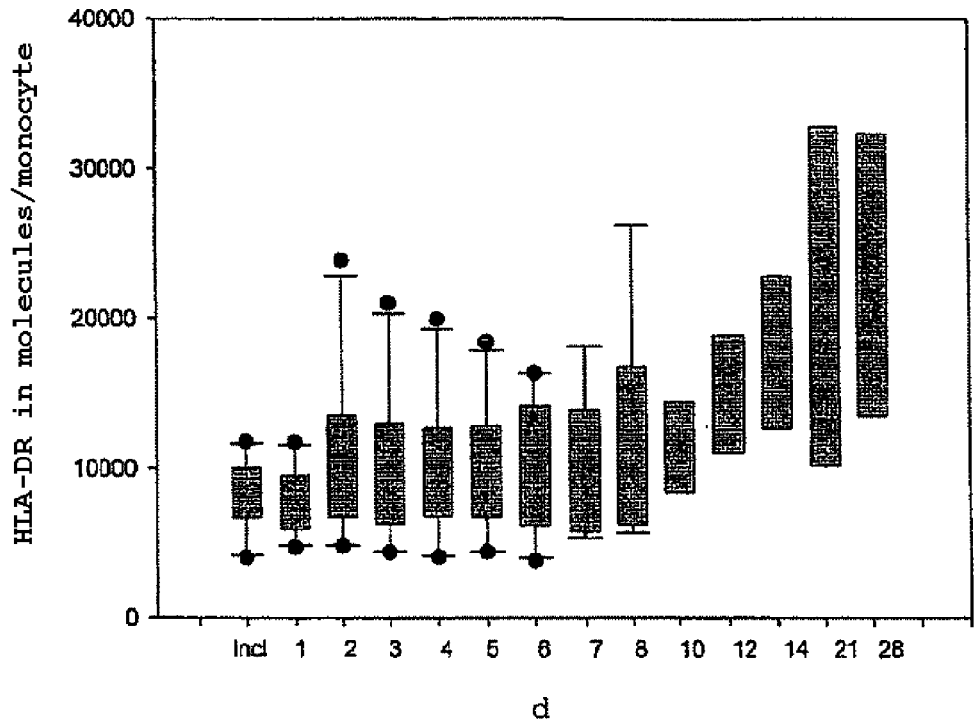

FIG. 5: 28-day course of the human leukocyte antigen (HLA)-DR value (HLA-DR molecules per monocyte) in ten patients with septic shock (from the day of the first treatment with the method according to the invention). Significant rise of pathological values to the normal range of values over the period shown.

Figure 6:
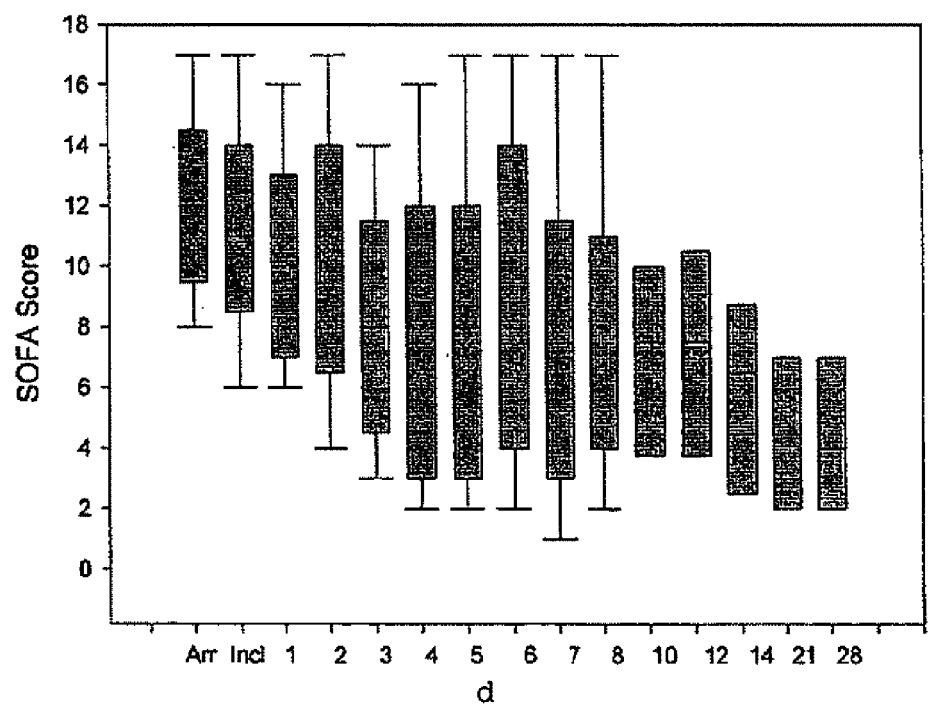

FIG. 6: 28-day course of the Sequential Organ Failure Assessment (SOFA) score value in ten patients with septic shock (from the day of the first treatment with the method according to the invention). Significant decrease of pathological values toward the normal range of value over the period shown.

REFERENCES

1. Thomas L (ed.) Labor and Diagnose. TH-Books Verlagsgesellsch.mbH, Frankfurt/Main, 5th ed. 2000 (ISBN 3-9805215-3-2)
2. Ronco C, Bellomo R (eds.): Critical Care Nephrology. Kluwer Academic Publishers Dordrecht, Boston, London 1998 (ISBN 0-7923-4610-6)
3. van de Kerkhove M P et al. Clinical application of bioartificial liver support systems. Ann Surg. 2004; 240: 216-30
4. Mitzner S R. Albumin dialysis: an update. Curr Opin Nephrol Hypertens. 2007; 16: 589-95
5. Lehmann H C et al. Plasma exchange in neuroimmunological disorders: part 2. Treatment of neuromuscular disorders. Arch Neurol. 2006; 63: 1066-71
6. Blessing F et al. Heparin-mediated extracorporeal low-density lipoprotein precipitation: rationale for a specific adjuvant therapy in cardiovascular disease. Transfus Apher Sci. 2004; 30: 255-66
7. Bellomo R et al: Extracorporeal blood treatment (EBT) methods in SIRS/Sepsis. Int J Artif Organs 2005; 28: 450-8
8. Ronco C, Inguaggiato P, D'Intini V, Cole L, Bellomo R, Poulin S, Bordoni V, Crepaldi C, Gastaldon F, Brendolan A, Trairak P, Khajohn T: The role of extracorporeal therapies in sepsis. J Nephrol. 16 Suppl 7: S34-S41, 2003.
9. Cole L, Bellomo R, Hart G, Journois D, Davenport P, Tipping P, Ronco C: A phase II randomized, controlled trial of continuous hemofiltration in sepsis. Crit Care Med. 30: 100-106, 2002.
10. Busund R, Koukline V, Utrobin U, Nedashkovsky E: Plasmapheresis in severe sepsis and septic shock: a prospective, randomised, controlled trial. Intensive Care Med. 28(10): 1434-1439, 2002.
11. Stegmayr B G, Banga R, Berggren L, Norda R, Rydvall A, Vikerfors T: Plasma exchange as rescue therapy in multiple organ failure including acute renal failure. Crit Care Med 31(6): 1730-1736, 2003.
12. Ronco C, Brendolan A, Lonnemann G, Bellomo R, Piccinni P, Digito A, Dan M, Irone M, La Greca G, Inguaggiato P, Maggiore U, De Nitti C, Wratten M L, Ricci Z, Tetta C: A pilot study of coupled plasma filtration with adsorption in septic shock. Crit Care Med. 30(6): 1250-1255, 2002.
13. Tetta C, Bellomo R, Ronco C: Artificial organ treatment for multiple organ failure, acute renal failure, and sepsis: recent new trends. Artif Organs 27(3): 202-213, 2003.
14. Vale J A, Rees A J, Widdop B, Goulding R: Use of charcoal haemoperfusion in the management of severely poisoned patients. Br med J I (1975) 5-9
15. O'Grady J G, Gimson A E S, O'Brien C J, Pucknell A, Hughes R D, Williams R: Controlled trials of charcoal hemoperfusion and prognostic factors in fulminant hepatic failure. Gastroenterol 94 (1988) 1186-1192
16. Weston M J, Gazzard B G, Buxton B H, Winch J, Flax H, Machado A L, Williams R: Effects of haemoperfusion through charcoal or XAD-2 resin on an animal model of fulminant liver failure. Gut 15 (1974) 482-486
17. Opolon P, Rapin J R, Huguet C, Granger A, Delorme M L, Boschat M, Sausse A: Hepatic failure coma (HFC) treated by polyacrylonitrile membrane (PAN) hemodialysis (HD). Trans Am Soc Artif Intern Organs 22 (1976) 701-708

18. Konstantin P, Chang J, Otto V, Brunner G: Artificial liver. Artif Organs 16 (1992) 235-242
19. Ash S R: Hemodiabsorption in treatment of acute hepatic failure and chronic cirrhosis with ascites. Artif Organs 18 (1994) 355-362
20. Bambauer R: Therapeutischer Plasmaaustausch and verwandte Plasmaseparationsverfahren. Schattauer, Stuttgart, New York, 1988, 182-189
21. Stanworth S J, Massey E, Hyde C, Brunskill S, Lucas G, Navarrete C, Marks D I: Granulocyte transfusions for treating infections in patients with neutropenia or neutrophil dysfunction. Cochrane Database Syst Rev 2005 (3): CD005339, 2005
22. Safdar A, Hanna H A, Boktour M, Kontoyiannis D P, Hachem R, Lichtiger B, Freireich E J, Raad I I: Impact of high-dose granulocyte transfusions in patients with cancer with candidemia: retrospective case-control analysis of 491 episodes of Candida species bloodstream infections. Cancer 101: 2859-2865, 2004.
23. Oberholzer A et al. Sepsis syndromes: understanding the role of innate and acquired immunity. Shock. 2001; 16: 83-96
24. Docke W D, Randow F, Syrbe U, Krausch D, Asadullah K, Reinke P, Volk H D, Kox W: Monocyte deactivation in septic patients: restoration by IFN-gamma treatment. Nat Med. 3(6): 678-681, 1997.
25. Caille V, Chiche J D, Nciri N, Berton C, Gibot S, Boval B, Payen D, Mira J P, Mebazaa A: Histocompatibility leukocyte antigen-D related expression is specifically altered and predicts mortality in septic shock but not in other causes of shock. Shock 22: 521-526, 2004.
26. Ploder M, Pelinka L, Schmuckenschlager C, Wessner B, Ankersmit H J, Fuerst W, Redl H, Roth E, Spittler A: Lipopolysaccharide-induced tumor necrosis factor alpha production and not monocyte human leukocyte antigen-DR expression is correlated with survival in septic trauma patients. Shock 25: 129-134, 2006.
27. Kaufmann I, Hoelzl A, Schliephake F, Hummel T, Chouker A, Peter K, Thiel M: Polymorphonuclear leukocyte dysfunction syndrome in patients with increasing sepsis severity. Shock 26: 254-261, 2006.

The invention claimed is:

1. A method for treating blood composition disorders and blood function disorders, comprising steps wherein
   a) blood plasma is acquired from the blood of a patient;
   b) the blood plasma of the patient is extracorporeally contacted with donor blood or modified donor blood wherein the donor blood or modified donor blood comprises at least $0.2\text{-}100 \times 10^{10}$ granulocytes per L, at least $1.0 \times 10^9$ thrombocytes per L, at least $1.0 \times 10^9$ erythrocytes per L, and blood plasma components, and wherein a mixture comprising (i) the patient's blood plasma and (ii) the donor blood or the modified donor blood is obtained by the contacting, which mixture comprises cells of the donor blood or modified donor blood; and
   c) blood plasma is separated from the cells of the mixture of step b) by means of a filtration step or a centrifugation step so that the blood plasma that is separated from the cells of the mixture can be supplied to the patient's blood, wherein the cells of the mixture are not administered to the patient.

2. The method of claim 1, wherein the donor blood or modified donor blood further comprises lymphocytes and/or monocytes.

3. The method of claim 1, wherein the blood plasma of the patient is extracorporeally contacted with modified donor blood in step b) and the modified donor blood comprises blood plasma.

4. The method of claim 1, wherein the blood plasma of the patient is extracorporeally contacted with modified donor blood in step b) and the modified donor blood comprises blood modified by volume restriction, leukocyte fraction enrichment, leukocyte depletion, erythrocyte depletion, depletion of antibodies, irradiation, coagulation inhibition, and/or stabilization.

5. The method of claim 1, wherein the blood plasma of the patient is extracorporeally contacted with modified donor blood in step b) and the granulocytes are enriched in the modified donor blood.

6. The method of claim 1, wherein the blood plasma from the patient's blood is acquired in step a) by setting up a pressure gradient over a semipermeable membrane or by centrifugation.

7. The method of claim 1, wherein the blood composition disorder or blood function disorder is a disorder selected from the group consisting of sepsis, severe sepsis, septic shock, renal insufficiency, renal failure, liver insufficiency, liver failure, immunodeficiency, and an infectious disease.

8. The method of claim 1, wherein the blood plasma of the patient is extracorporeally contacted with modified donor blood in step b) and the modified donor blood has been generated from donor blood by at least one method selected from the group consisting of volume restriction; leukocyte fraction enrichment; depletion of one or more of leukocytes, individual leukocyte types, erythrocytes, and antibodies; irradiation; and addition of one or both of coagulation inhibiting substances and stabilizers.

9. The method of claim 7, wherein the blood composition disorder or blood function disorder is sepsis in the phase of immunoparalysis, severe sepsis in the phase of immunoparalysis, or septic shock in the phase of immunoparalysis.

10. The method of claim 8, wherein the blood plasma of the patient is extracorporeally contacted with modified donor blood in step b) and the modified donor blood has been generated from donor blood by partial plasma withdrawal.

11. The method of claim 3, wherein the blood plasma of the patient is extracorporeally contacted with modified donor blood in step b) and the modified donor blood comprises physiological saline solution.

12. The method of claim 1, wherein the blood plasma of the patient is extracorporeally contacted with modified donor blood in step b) and the modified donor blood comprises physiological saline solution.

* * * * *